United States Patent [19]

Cousse et al.

[11] Patent Number: 4,734,417

[45] Date of Patent: Mar. 29, 1988

[54] LIPID- AND CHOLESTEROL-REDUCING DERIVATIVES OF HALO-BIPHENYL PRIMARY ALCOHOLS

[75] Inventors: Henri Cousse; André Delhon; Jean-Pierre Rieu; Gilbert Mouzin, all of Castres, France

[73] Assignee: P.F. Medicament, Paris, France

[21] Appl. No.: 882,586

[22] Filed: Jul. 7, 1986

[30] Foreign Application Priority Data

Jul. 8, 1985 [FR] France ................. 85 10528

[51] Int. Cl.$^4$ ................. A61K 31/495; C07D 295/00; C07D 213/80
[52] U.S. Cl. ................. 514/255; 514/356; 514/400; 544/399; 546/318; 546/322; 548/341
[58] Field of Search ............ 544/399; 546/318, 322; 548/341; 514/255, 356, 400

[56] References Cited

FOREIGN PATENT DOCUMENTS 8096019 6/1983 Japan ................. 514/255
11483 1/1985 Japan ................. 514/255

OTHER PUBLICATIONS

Chisso Corp., CA 98-71716k.
Imperial Chem. Industrial, CA 105-114745j.
Mozin et al, CA 98-34378t.
Moore et al, CA 96-117265p, 117266q and 117267r.
Bowie, CA 96-85252p.
C. H. Brieskorn et al, CA 63-13115e.

*Primary Examiner*—Donald G. Daus
*Assistant Examiner*—Cecilia Shen

*Attorney, Agent, or Firm*—Gordon W. Hueschen

[57] ABSTRACT

The invention relates to new derivatives of biphenyl primary alcohols, their preparation and use as medicaments useful in the treatment and prevention of atherosclerotic disorders. The new derivatives have the general formula

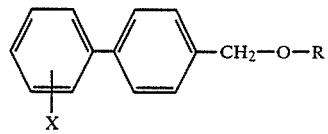

in which X represents a halogen atom, and more particularly chlorine, bromine or fluorine in ortho or meta position, R represents an alkyl, amino alkyl, pyridyl alkyl or acyl radical and more particularly

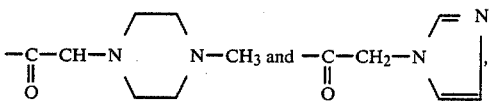

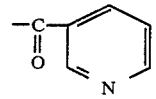

and acetyl.

8 Claims, No Drawings

LIPID- AND CHOLESTEROL-REDUCING DERIVATIVES OF HALO-BIPHENYL PRIMARY ALCOHOLS

The present invention relates to new derivatives of halo-biphenyl primary alcohols having lipid-reducing and cholesterol-reducing properties, the method of preparing them and their use as medicaments useful for the treatment and prevention of the atherosclerotic disorders.

In French Pat. Nos. 2,476,072 and 2,498,449, filed by the present applicant, reference is had to derivatives of halo-biphenyl carboxylic acid which are useful for the treatment of disorders caused by atherosclerosis.

The new compounds discovered by the applicant have a different structure due to the presence of an ether or ester functional group.

The object of the invention is derivatives of halo-biphenyl alcohols of the general formula

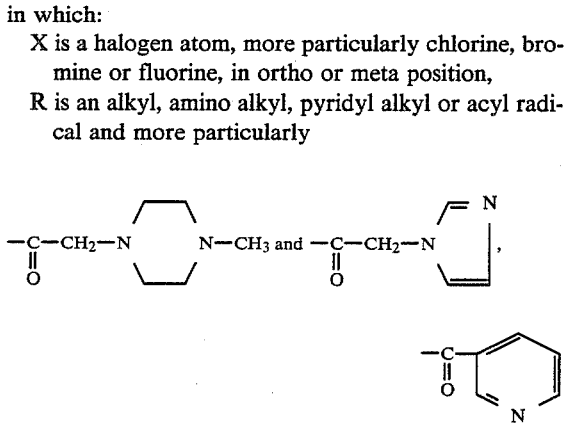

in which:

X is a halogen atom, more particularly chlorine, bromine or fluorine, in ortho or meta position, R is an alkyl, amino alkyl, pyridyl alkyl or acyl radical and more particularly and acetyl.

The invention also concerns the salts of compounds of formula I in the event that R is salifiable with therapeutically acceptable inorganic or organic acids.

The invention also relates to a method of preparing derivatives of formula I by reacting of primary alcohols of formula II

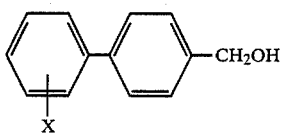

in which X has the same meaning as in formula I, with a compound of the formula $R_nY$ in which R has the same meaning as in formula I and Y represents a halogen atom (n=1) or the sulfate function (n=2), in accordance with the reaction mechanism:

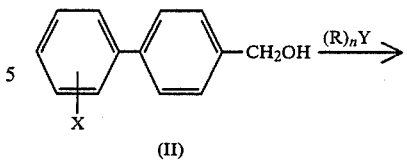

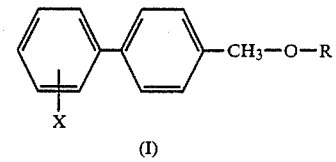

The present invention also concerns the use of the compounds of formula I as medicament, as well as pharmaceutical compositions containing these medicaments.

The pharmaceutical compositions of the present invention may comprise one or more compounds of formula I, possibly combined with other active principles.

Among the derivatives of formula I, the following derivatives may more particularly be mentioned:

EXAMPLE 1

4-(3-pyridyl methoxymethyl)-2'-chlorobiphenyl hydrogenoxalate (F 2832)

A mixture of 4-(2'-chloro biphenyl)-methanol (7 g, 32 mmols) and tetrabutylammonium hydrogen sulfate (2.17 g, 64 mmols) is stirred at ordinary temperature in a 50% solution of caustic soda (25.6 g). Nicotinyl chloride hydrochloride (15.75 g, 96 mmols) is added in separate portions, whereupon the agitation is continued for six hours. The mixture, poured into ice water, is extracted with ether (2×250 ml), washed with water (3×200 ml) and saline solution (20 ml) and dried over sodium sulfate.

After concentration in vacuum and filtration over silica gel (250 g elution: chloroform/methanol 95:5) 7.8 g of product are isolated. The base obtained, extracted in isopropanol, is salified with oxalic acid (2 g/100 ml of isopropanol).

The derivative of the formula:

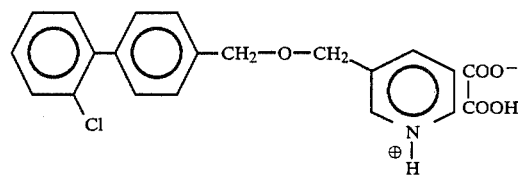

is isolated in a yield of 50%.

Empirical formula: $C_{21}H_{18}ClNO_5$
Molecular weight: 399.83
Melting point: 108° C.
Thin-layer chromatography:
support: silica gel 60 F 254 Merck
solvent: $CHCl_3$-MeOH 95/5
development: UV and iodine
Rf: 0.50
Solubility: 0.1% in water.

The following examples were prepared in a manner similar to that described in Example 1:

EXAMPLE 2

4-(methoxy methyl)-2'-chloro biphenyl (F 2816)

4-(2'-chloro biphenyl)methanol treated with methyl sulfate leads to the derivative of the formula:

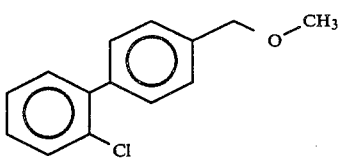

Empirical formula: $C_{14}H_{14}ClO$
Molecular weight: 232.71
Boiling point: 130° C./$10^{-3}$ mm-$n_D^{26}$: 1.5902
Thin-layer chromatography:
support: silica gel 60 F 254 Merck
solvent; hexane/ethyl-acetate 70:30
development: UV
Rf: 0.60
Solubility: 1% in propylene glycol

EXAMPLE 3

4-(ethoxymethyl)-2'-chloro biphenyl (F 2815)

By the method of Example 1, replacing the nicotinyl chloride by ethyl bromide, there is obtained the derivative having the structure:

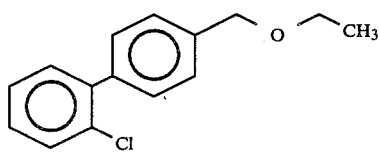

Empirical formula: $C_{15}H_{15}ClO$
Molecular weight: 246.74
Boiling point: ($10^{-3}$ mm) 160° C. -$nD^{25}$: 1.5760
Thin-layer chromatography:
support: silica gel 60 F 254 Merck
solvent: hexane/ethyl-acetate 70:30
development: UV
Rf: 0.61
Solubility: 0.6% in propylene glycol

EXAMPLE 4

4-(n-butoxy methyl)-2'-chloro biphenyl (F2831)

The treatment of 4-(2'-chloro biphenyl)methanol with butyl bromide by the method of Example 1 leads to the derivative of the structure:

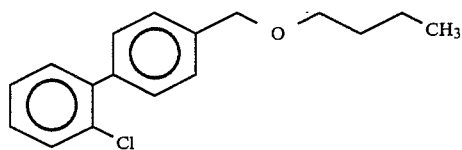

Empirical formula: $C_{17}H_{19}ClO$
Molecular weight: 274.79
Boiling Point ($10^{-3}$ mm): 160° C.-$nD^{22}$: 1.5640
Thin-layer chromatography:
support: silica gel 60 F 254 Merck
solvent: hexane/ethyl-acetate 70:30
development: UV
Rf: 0.70
Solubility: 0.3% in propylene glycol.

In the same manner, starting from the appropriate lower-alkyl bromide, other 4-(lower-alkyloxymethyl) compounds are prepared.

EXAMPLE 5

4-[(2-dimethylamino ethoxy)methyl]2'-chloro biphenyl hydrogen oxalate (F 2856)

A mixture of 4-(2'-chloro biphenyl)methanol (7 g, 30 mmols) and 2-diethylamino ethylchloride hydrochloride (13.05 g, 90 mmols) is cooled on an ice bath and then treated with agitation with 16.1 ml of 50% caustic soda solution (0.3 mol). Agitation is maintained for 24 hours at room temperature, whereupon the reaction mixture is poured into cold water and extracted with ether (2×100 ml).

The ether phase is washed with water (3×100 ml) and then with saline solution (150 ml), dried over sulfate and evaporated in vacuum. The phase obtained (8.5 g), extracted in ethyl acetate, is salified by a solution of oxalic acid in ethyl acetate (2.65 g/100 ml). The crystals obtained, after filtration, centrifuging and drying, are recystallized from isopropyl ether (320 ml). The compound

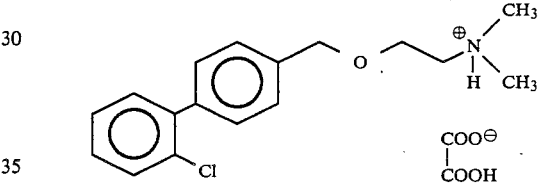

is isolated in a yield of 65%.
Empirical formula: $C_{19}H_{22}ClNO_5$
Molecular weight: 379.84
Melting point: 138.5° C.
Thin-layer chromatography:
support: silica gel 60 F 254 Merck
solvent: $CHCl_3$-MeOH-$NH_4OH$
developer: UV and iodine Rf: 0.50
Solubility: 0.25% in water.

In the same manner, other 2-lower-alkylaminoethoxy compounds are prepared, starting with the selected 2-dilower-alkylaminoethyl chloride or bromide.

EXAMPLE 6

4-[(4-methyl (1-4) 1-piperazinyl)acetoxymethyl]2'-chloro biphenyl (F 2876)

1. Preparation of 2'-chloro 4-(chloroacetoxymethyl)-biphenyl 4-(2'-chloro biphenyl)methanol (15 g, 68.5 mmols) in DMF (150 ml) is treated, drop by drop, at a temperature of 0° C. with chloracetyl chloride (8.5 g, 75.3 mmols).

After stirring for one hour at room temperature, the solution is poured into ice water, extracted with ether (200 ml), washed with water (6×200 ml) and dried over sulfate.

The solution is evaporated to dryness under vacuum (Wt=20 g).

2. Condensation of the amine

A solution of the preceding derivative (10 g, 34 mmols) in 100 ml of DMF is cooled to 0° C. and then treated with monomethyl piperazine (13.6 g, 136 mmols). The mixture is maintained under agitation at room temperature for one hour and then poured onto ice water (400 ml). The organic base is extracted with ether (2×200 ml), washed with water (5×200 ml), with bicarbonate (100 ml) and then with saline solution (2×100 ml). Upon drying over sulfate and evaporation in vacuum 10.8 g of product are obtained.

The base, extracted in isopropyl alcohol (500 ml), is added to a solution of maleic acid in isopropyl alcohol (7 g/150 ml). The crystals obtained, after centrifuging and drying, are recrystallized in a 90:10 isopropanol/ethanol mixture.

The compound

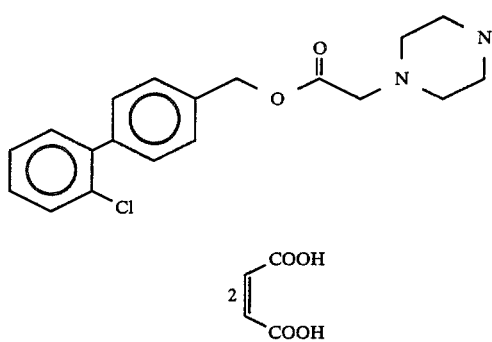

is isolated in a yield of 60%.
Empirical formula: $C_{28}H_{31}ClN_2O_{10}$
Molecular weight: 591.01
Melting point: 153° C.
Thin-layer chromatography:
support: silica gel 60 F 254 Merck solvent: $CHCl_3$-$MeOH$-$NH_4OH$ 90:9:1
developer: UV and iodine
Rf: 0.50
Solubility: 0.25% in water.

EXAMPLE 7

4-(imidazolyl acetoxy methyl)2'-chloro biphenyl hydrogen maleate (F 2875)

A solution of 2'-chloro 4-(chloroacetoxymethyl)-biphenyl (10 g, 34 mmols) obtained in accordance with Example 6.1, in solution in DMF (100 ml), is treated at 0° C. with imidazole (9.25 g, 136 mmols) and then with triethylamine (12 ml).

The mixture is stirred for 24 hours at room temperature and then poured onto ice water. After extraction with ether (2×250 ml), washing with water (5×200 ml), with bicarbonate (2×100 ml) and then with saline solution, the organic phase is dried over sulfate and concentrated in vacuum (Wt=8.75 g). The base, taken up in isopropanol (100 ml), is added to a solution of maleic acid (3.1 g/100 ml of isopropanol). After crystallization in the cold, the product is recrystallized from isopropanol (100 ml).

The compound of the formula

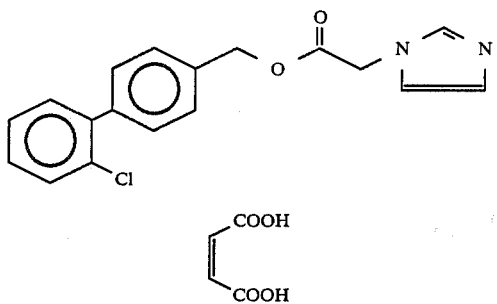

is obtained in a yield of 63%.
Empirical formula: $C_{22}H_{19}ClN_2O_6$
Molecular weight: 442.855
Melting point: 103° C.
Thin-layer chromatography:
support: silica gel 60 F 254 Merck
solvent: $CHCl_3$-$MeOH$-$NH_4OH$ 90:9:1
developer: UV and iodine
Rf: 0.60
Solubility: 0.5% in water.

EXAMPLE 8

4-(3-pyridyl carboxymethyl)-2'-chloro biphenyl (F 2882)

A solution of nicotinic acid (16.9 g, 137 mmols) in pyridine (120 ml) is treated, drop by drop, with thionyl chloride (16.3 g, 137 mmols) at room temperature. After stirring overnight, the 4-(2'-chloro biphenyl)methanol is added and it is set aside for an additional 24 hours with agitation.

After evaporation of the pyridine and dissolving with water, the pH is brought to 6 and the solution extracted with ether (3×100 ml). The ether phase is washed with water (2×100 ml), with 10% citric acid (2×100 ml) and with saline solution and then dried over sulfate and concentrated in vacuum.

The crude product is extracted with 1/10N hydrochloric acid (50 ml) and precipitated with 2 parts by volume of water. After recrystallization in a 75:25 cyclohexane/isopropyl-ether mixture, the compound

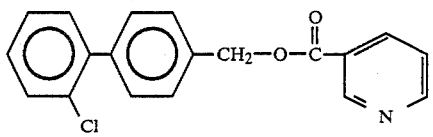

is obtained in a yield of 62%.
Empirical formula: $C_{19}H_{14}ClNO_2$
Molecular weight: 323.78
Melting point: 65° C.
Thin-layer chromatography:
support: silica gel 60 F 254 Merck
solvent: hexane/ethyl acetate 50:50
developer: UV and iodine
Rf: 0.35
Solubility: 0.5% in propylene glycol.

EXAMPLE 9

Acetoxy 4-methyl 2'-chloro biphenyl (F 2855)

A solution of 4-(2'-chloro biphenyl)methanol (6 g, 27 mmols) and acetyl chloride (2.76 g, 35 mmols) in ether (70 ml) is treated, drop by drop, at 0° C., with triethylamine (4.35 g, 43 mmols). After agitating for 3 hours at room temperature, the ether phase is filtered, washed with 1N caustic soda, with water and then with saline solution. After drying over sulfate, the filtrate is evaporated in vacuum and the residual oil rectified under vacuum to give the compound:

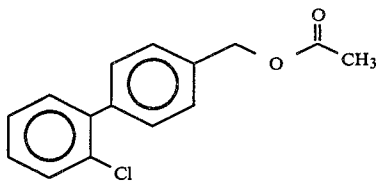

in a yield of 92%.
Empirical formula: $C_{15}H_{13}ClO_2$
Molecular weight: 260.72
Boiling point (4.10$^{-3}$ mm Hg): 160° C.-$n_D^{22}$: 1.5825
Thin-layer chromatography:
support: silica gel 60 F 254 Merck
solvent: hexane/ethyl acetate 70:30
developer: UV and iodine
Rf: 0.60
Solubility: 1% in propylene glycol Other lower-acyloxy compounds are prepared in the same manner starting with the appropriate lower-acyl-chloride or other replaceable halide, such as the bromide.

EXAMPLE 10

2'-chloro 4-(diethylamino acetoxymethyl)biphenyl hydrogen maleate (F 2870)

In a manner similar to Example 7, the intermediate 2'-chloro 4-(chloroacetoxymethyl)biphenyl (9.1 g, 32 mmols) treated with diethylamine leads to the derivative of the formula:

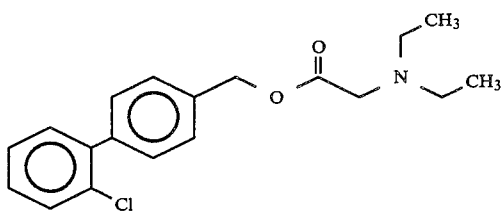

Empirical formula: $C_{23}H_{26}ClNO_6$
Molecular weight: 447.915
Melting point: 104° C.
Thin-layer chromatography:
support: silica gel 60 F 254 Merck
solvent: $CHCl_3$-MeOH 95/5
developer: UV and iodine
Rf: 0.50
Solubility: 0.33% in water.

Other lower-alkylamino and dilower-alkylamino compounds are prepared in the same manner starting from the appropriate lower-alkylamine or dilower-alkylamine.

EXAMPLE 11 TO 15

In a manner similar to that described in Example 1, using the corresponding alcohols and halogen derivatives, the following compounds were preapred:

| EXAMPLES | CHEMICAL FORMULA |
|---|---|
| Example 11 | 4-(3-pyridyl methoxymethyl) 2'-fluoro biphenyl |
| Example 12 | 4-(3-pyridyl methoxymethyl) 3'-chloro biphenyl hydrochloride |
| Example 13 | 4-(ethoxymethyl) 3'-chloro biphenyl |
| Example 14 | 4-(ethoxymethyl) 3'-bromo biphenyl |
| Example 15 | Acid oxalate of 4-(3-pyridyl methoxymethyl) 2'-bromo biphenyl |

Those compounds of the present invention wherein the group R is a salt-forming group can be administered to man or animal orally or parenterally in the form either of the free base or in the form of a therapeutically-acceptable salt. The new derivatives which are bases can be converted into acid addition salts with acids, which acid addition salts form part of the invention. These acid addition salts can be obtained by reaction of the new basic derivatives with an acid in a suitable solvent, such as for example, in the mineral acid series,, hydrochloric, hydrobromic, methanesulphonic, sulphuric, and phosphoric, and in the organic series, acetic, propionic, maleic, fumaric, tartaric, citric, oxalic, and benzoic acid, to name only a few. The selection of the free base or acid addition salt thereof in preparation of the desired acid addition salt in any particular case will be apparent and fully within the capability of one skilled in the art. Such novel compounds of the invention are frequently used in the form of their pharmaceutically-acceptable acid addition salts, such as the hydrochlorides, hydrobromides, or the like, since the salt form is usually the best form for pharmaceutical formulations. Innumerable other pharmaceutically-acceptable acid addition salts can be prepared from the hydrochlorides or other acid addition salts via the free bases in conventional manner.

EXPERIMENTS

Various toxicological and pharmacological tests were carried out on the compounds forming the object of the invention.

(A) Toxicology

The compounds of the present invention were subjected to toxicity studies. The toxicity of the compounds was determined by the $LD_{50}$. It was examined on lots of 10 mice orally and intravenously and calculated in accordance with the method of MILLER and TAINTER (Proc. Soc. Exper. Biol. Med., 1944, 57, 261). The $LD_{50}$ of the compounds tested is greater than 100 mg/kg intravenously and 1000 mg/kg orally.

(B) Pharmacological Properties

The pharmacological experiments made it possible to show establish remarkable lipid-reducing and cholesterol-reducing properties. Verification was confirmed by several tests.

The results obtained with the products of Examples 1, 6 and 7 are reported below, compared with CLOFIBRATE and FENOFIBRATE.

Test covering 4 days of oral administration by the method of BUCHNAN, SPRANCMANIS and PARTYKA (J. Med. Chem., 12, 1001-1006 1969). Male rats, unconditioned, Sprague Dawley, divided into homogeneous lots of 8 animals each.

Treatment orally by the products to be studied in solution or suspension in 1% CMC in a volume of 10 ml/kg.

Duration of treatment: 4 days.

Frequency of treatments: Once a day.

On the fifth day, sampling of blood with heparin from caudal artery, after fasting for about 16 hours.

The results are set forth in the following table compared with CLOFIBRATE and FENOFIBRATE

| Product | Dose mg/kg/day | Cholesterol, % decrease referred to control | Consumption of food % variation referred to control |
|---|---|---|---|
| CLOFIBRATE | 100 | −17 | −14 |
|  | 200 | −8 (NS) | −10 |
|  | 300 | −12 (−NS) | −40 |
| FENOFIBRATE | 100 | −16 | −23 |
|  | 200 | −27 | −10 |
|  | 300 | −25 | −17 |
| EXAMPLE 1 | 25 | −5 (−NS) | −57 |
|  | 50 | −24 | −63 |
| F 2832 | 100 | −62 | −64 |
| EXAMPLE 6 | 25 |  | −30 |
|  | 50 | −27 | −41 |
| F 2876 | 100 | −75 | −76 |
| EXAMPLE 7 | 25 | −35 | −43 |
|  | 50 | −51 | −52 |
| F 2875 | 100 | −77 | −46 |

(C) Therapeutic Applications

Based on their pharmacological properties, the compounds of the invention, and more particularly the compounds of Examples 1, 6 and 7, can be used in therapy for the treatment of the different types of hyperlipidemias for the prevention and treatment of atherosclerosis.

The pharmaceutical preparations containing these active principles can be administered orally or parenterally.

It is possible to combine other pharmaceutically and therapeutically acceptable active principles with them.

In conclusion, from the foregoing, it is apparent that the present invention provides novel compounds which are useful for their lipid- and cholesterol-reducing properties, a process for the production thereof, pharmaceutical compositions comprising the same, and a method of treating a subject in need of such lipid-reduction and/or cholesterol-reduction by treating the said subject with a lipid-reducing and cholesterol-reducing amount of a compound of the invention, all of the foregoing compounds, process, compositions, and method of treating having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

What is claimed is:

1. Heterocyclic ester or ether of a halo-biphenyl primary alcohol having the formula (I):

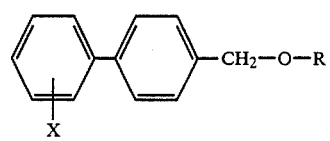

in which:

X represents a halogen atom in ortho or meta position
R represents a pyridyl methyl radical or an acyl radical selected from

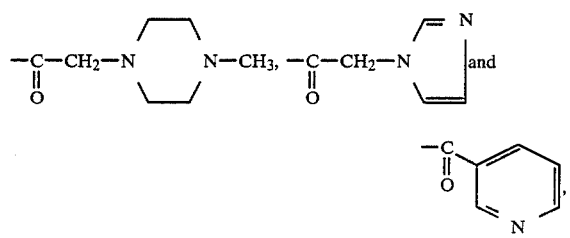

and, in the event that R is salifiable, therapeutically acceptable salts thereof with inorganic or organic acids.

2. A compound according to claim 1, selected from among:

4-(3-pyridyl methoxymethyl)2′-chloro biphenyl hydrogen oxalate (F 2832)

4-[(4-methyl 1-piperazinyl) acetoxymethyl]2′-chloro biphenyl dihydrogen maleate (F 2876)

4-(imidazolyl acetoxymethyl) 2′-chloro biphenyl hydrogen maleate (F 2875)

4-(3-pyridyl carboxymethyl) 2′-chloro biphenyl (F 2882)

4-(3-pyridyl methoxymethyl) 2'-fluoro biphenyl hydrochloride 4-(3-pyridyl methoxymethyl) 3'-chloro biphenyl hydrochloride, and acid oxalate of 4-(3-pyridyl methoxymethyl) 2'-bromo biphenyl.

3. Pharmaceutical composition useful for cholesterol- and lipid-reduction, characterized by the fact that as active principle it contains at least one compound according to claim 1 in cholesterol- or lipid-reducing amount.

4. Pharmaceutical composition according to claim 3, characterized by the fact that it is adapted to be administered orally or parenterally.

5. A method of lipid reduction and cholesterol reduction in a subject in need thereof which comprises the step of administering to the said subject a lipid-reducing and cholesterol-reducing amount of a compound of claim 1.

6. Method for cholesterol or lipid reduction in a subject in need of the same, comprising the step of administering to said subject an effective cholesterol- or lipid-lowering amount of a compound of claim 1.

7. Method of claim 6, wherein the compound is a compound of claim 2.

8. Method of claim 6, wherein the compound is administered orally or parenterally.

* * * * *

UNITED STATES PATENT AND TRADEMARK OFFICE
CERTIFICATE OF CORRECTION

PATENT NO. : 4,734,417

DATED : March 29, 1988

INVENTOR(S) : Henri Cousse, André Delhon, Jean-Pierre Rieu and Gilbert Mouzin

It is certified that error appears in the above-identified patent and that said Letters Patent is hereby corrected as shown below:

Col. 4, line 45; "Rf: 0.50" should be on a separate line below this line

Col. 5, line 40; "solvent: $CHCl_3$-" should be on the line below this line and should read
-- solvent: $CHCl_3$-MeOH-$NH_4$OH 90:9:1 --

Signed and Sealed this

Twenty-seventh Day of December, 1988

Attest:

DONALD J. QUIGG

Attesting Officer      Commissioner of Patents and Trademarks